United States Patent [19]
Burkhardt et al.

[11] Patent Number: 6,048,985
[45] Date of Patent: Apr. 11, 2000

[54] BORANE-TETRAHYDROFURAN COMPLEX METHOD OF STORING AND REACTING BORANE-TETRAHYDROFURAN COMPLEX

[75] Inventors: Elizabeth R. Burkhardt, Bridgeville; Joseph A. Corella, II, Wexford, both of Pa.

[73] Assignee: Mine Safety Appliances Company, Pittsburgh, Pa.

[21] Appl. No.: 09/218,914

[22] Filed: Dec. 22, 1998

[51] Int. Cl.[7] .............................. C07D 307/06; C09K 3/00
[52] U.S. Cl. ..................... 549/213; 252/188.1; 149/22; 423/294; 568/1
[58] Field of Search .................... 252/188.1; 549/213; 149/22; 423/294; 568/1

[56] References Cited

PUBLICATIONS

H. C. Brown, P. Heim, N. M. Yoon *JACS*, 1970, 92, pp. 1637–1646. "Selective Reductions. XV. Reaction of Diborane in Tetrahydrofuran With Selected Organic Compounds Containing Representative Functional Groups".

J. R. Elliott, W. L. Roth, G. F. Roedel and E. M. Boldebuck *JACS* 1952, 74, pp. 5211–5212, "Solubility of Diborane– and Boron–containing Lithium Salts".

B. Rice, J. A. Livasy, G. W. Schaeffer *JACS* 1955, 77, p. 2750. "Tetrahydrofuran–Borine".

H. E. Wirth, F. E. Massoth, D. X. Gilbert *J. Phys. Chem.* 1958, 52, pp. 870–871. "Complexes of Ethers With Diborane".

C. F. Lane *Chem. Rev.* 1976, 76, pp. 773–799 "Reduction of Organic Compounds With Diborane".

H. C. Brown, M. C. Desai, P. K. Jadhav *JOC* 1982, 47, pp. 5065–5069 "Hydroboration. 61. Diisopinocampheylborane of High Optical Purity. Improved Preparation and Asymmetric Hydroboration of Representative Cis–Disubstituted Alkenes".

M. Follet *Chem. and Industry* 1986, pp. 123–128 "Use of Complexes of Diborane and Organoboranes on a Laboratory and Industrial Scale".

K. Smith *Chem. and Industry* 1987, pp. 603–611. "Advances in Organoboron Chemistry—Prospects for Industry".

*Primary Examiner*—John Kight
*Assistant Examiner*—Charanjit S. Aulakh
*Attorney, Agent, or Firm*—James G. Uber; Henry E. Bartony, Jr.

[57] ABSTRACT

A method of stabilizing borane-tetrahydrofuran complex comprises the step of maintaining the temperature of the borane-tetrahydrofuran complex at or below 20° C. A method of reacting a borane reagent with a substrate comprises the steps of heating the borane reagent and the substrate in a reaction vessel and preventing escape of evolved diborane from the reaction vessel. Preferably, a reaction vessel containing a borane reagent and a substrate is maintained under at greater than atmospheric pressure with back-pressure regulation.

20 Claims, 4 Drawing Sheets

BORANE-TETRAHYDROFURAN COMPLEX METHOD OF STORING AND REACTING BORANE-TETRAHYDROFURAN COMPLEX

FIELD OF THE INVENTION

The present invention relates to borane-tetrahydrofuran complexes and to methods of storing and reacting borane-tetrahydrofuran complexes and, more particularly, to relatively highly concentrated borane-tetrahydrofuran complexes and to methods of storing and reacting borane-tetrahydrofuran complexes that reduce waste thereof.

BACKGROUND OF THE INVENTION

Borane-tetrahydrofuran complex (sometimes referred to as THFB) is a valuable reagent for the reduction of functional groups and for hydroboration reactions with carbon-carbon double and triple bonds. Functional groups reduced by borane-tetrahydrofuran complex include aldehyde, ketone, acyl chloride, lactone, epoxide, ester, amide, oxime, imine, and nitrile. Borane-tetrahydrofuran complex is a very selective and efficient reducing agent. Typically a reduction is quenched with excess methanol to deactivate any remaining borane-tetrahydrofuran complex and distilled to remove the boron from the desired products as the methylborate/methanol azeotrope.

Unfortunately, borane-tetrahydrofuran complex has been commercially available only as 1 molar solutions for a number of years. In the interest of conservation of resources and efficient use of reactor vessels, however, one would like to conduct reactions at the highest concentration possible for a particular reaction. In that regard, the low concentration of the borane-tetrahydrofuran complex leads to low reactor loading and inefficient use of equipment.

Other more concentrated borane reagents are available but each has inherent disadvantages. For example, sulfide boranes are highly concentrated but suffer from noxious odors. Concentrated amine boranes are also available, but are often not sufficiently reactive to reduce the desired functional groups. In addition, such complexing agents (amine or sulfide) are often difficult to remove from the desired product. Diborane typically requires cryogenic storage conditions (for example, less than $-100°$ C.) to maintain high purity.

In U.S. Pat. No. 3,634,277, Brown demonstrated that borane-tetrahydrofuran complex could be somewhat stabilized from ring-opening ether cleavage of the tetrahydrofuran (THF) by the addition of borohydride or use of excess borohydride in the synthesis. The THFB solutions of U.S. Pat. No. 3,634,277 were made by an in situ process of generating the borane from excess sodium or potassium borohydride and boron trifluoride. Although a range is not given for the concentrations of THFB stabilized by borohydride in U.S. Pat. No. 3,634,277, all the examples thereof described concentrations of 1.5 to 2.0 M THFB. Shelf-life/stability experiments were conducted at ambient temperature for eight weeks. Significant decomposition of the borane-tetrahydrofuran complex was observed even over that short time span.

Notwithstanding the disclosure in U.S. Pat. No. 3,634,277 of the synthesis of relatively highly concentrated borane-tetrahydrofuran complex, Brown and others in the literature have indicated that solutions of borane-tetrahydrofuran complex of greater than 1 M are unavailable as a result of the instability of such solutions. See, for example, H. C. Brown, P. Heim, N. M. Yoon *JACS*, 92, 1637–1646 (1970); C. F. Lane *Chem. Rev.*, 76, 773–799 (1976); H. C. Brown, M. C. Desai, P. K. Jadhav *JOC*, 47, 5065–5069 (1982); M. Follet *Chem. And Industry.*, 123–128; and K. Smith, *Chem. and Industry* 1987, 603–611 (1986).

In addition to decomposing during storage, borane-tetrahydrofuran complexes also thermally decompose in the course of reaction thereof at elevated temperatures. To achieve complete reduction of a functional group, excess borane-tetrahydrofuran complex is typically required. Use of excess borane reagent adds to the cost of the desired reduction and can lead to impurity formation. It is desirable to use only the stoichiometric amount of reducing agent both from the financial and environmental standpoints.

It is, therefore, very desirable to develop compositions and methods to achieve more efficient use of borane-tetrahydrofuran complex.

SUMMARY OF THE INVENTION

In general, the present invention provides a method of stabilizing a borane-tetrahydrofuran complex. The method comprises the step of maintaining the temperature of the borane-tetrahydrofuran complex at or below approximately $20°$ C. Preferably, however, the temperature of the borane-tetrahydrofuran complex is maintained above cryogenic temperatures, which are typically defined as temperatures below approximately $-78°$ C. More preferably, the temperature is maintained in the range of approximately $-40°$ C. to $20°$ C. More preferably, the temperature is maintained in the range of approximately $-20°$ C. to $20°$ C. More preferably, the temperature is maintained in the range of approximately $-20°$ C. to $15°$ C. Even more preferably, the temperature is maintained below approximately $5°$ C. Most preferably, the temperature is maintained in the range of approximately $-20°$ C. to $5°$ C.

Preferably the borane-tetrahydrofuran complex has a relatively high concentration of borane-tetrahydrofuran complex per liter of tetrahydrofuran, for example, above 0.9 M. Preferably, the concentration of borane-tetrahydrofuran complex per liter of tetrahydrofuran is at least 1.0 M. More preferably, the concentration of borane-tetrahydrofuran complex per liter of tetrahydrofuran is at least 1.5 M. Even more preferably, the concentration is at least 2.0 M.

Surprisingly, it has been discovered that the moderately low temperatures used in the present invention retard the ether cleavage of THF by borane or THFB. High purity of THFB can thus be preserved/stored for at least several years, enabling timely delivery of a higher purity product than previously possible. Moreover, analytical analysis of such THFB need not be repeated before shipment or use. Furthermore, no pressure increase occurs in the stored cylinders.

Numerous advantages are afforded by the ability to use relatively highly concentrated borane-tetrahydrofuran complex in reactions. For example, these advantages include lower shipping costs; more efficient use of reactor vessels, resulting in lower production cost; easier handling than required with diborane; and lack of a noxious odor associated with other borane reagents.

The borane-tetrahydrofuran complexes of the present invention are preferably made in high purity by addition of diborane to the solvent, tetrahydrofuran, rather than via an in situ synthetic route. Advantages of producing the borane-tetrahydrofuran complex by addition of diborane to tetrahydrofuran include avoidance of sodium tetrafluoroborate ($NaBF_4$) filtration during synthesis; a consistent quantity of sodium borohydride added as a stabilizer; a homogeneous reaction medium; and avoidance of boron trifluoride ($BF_3$) complexes and by-products generated from $BF_3$.

The present invention also provides a borane-tetrahydrofuran complex in which the concentration of borane-tetrahydrofuran complex per liter of tetrahydrofuran is greater than 1.0 M and the temperature of the complex is within the ranges discussed above. Preferably, the temperature is in the range of approximately −20° C. to approximately 20° C. Most preferably, the temperature is maintained in the range of approximately −20° C. to 5° C.

The present invention further provides a method of reacting a borane reagent with a substrate (that is, a compound to be reacted with the borane reagent), the method comprising the step of heating the borane reagent and the substrate in a reaction vessel and preventing the escape of evolved gaseous diborane from the reaction vessel. Preventing at least some of diborane from escaping the reaction vessel will increase the efficiency of the reaction.

Preferably, a reaction vessel containing a borane reagent and a substrate is maintained with a back-pressure regulator at a pressure greater than approximately atmospheric pressure (0 psig). More preferably, the pressure is in the range of approximately 5 to approximately 100 psig. Even more preferably, the pressure is in the range of approximately 5 to approximately 50 psig. Most preferably, the pressure is in the range of approximately 10 to approximately 40 psig.

As used herein, the term "borane reagent" refers generally to any reagent comprising a BH, $BH_2$ or a $BH_3$ complex that evolves gaseous diborane. Such evolution of gaseous diborane is typically accelerated at elevated temperature. Such boron reagents include amine boranes, sulfide boranes and ether boranes. Preferably, the borane reagent is borane-tetrahydrofuran complex (an ether borane).

Preferably, the borane-tetrahydrofuran complex has a concentration of borane-tetrahydrofuran complex per liter of tetrahydrofuran of at least 1 M and the borane-tetrahydrofuran is stored before reaction thereof at reduced temperature as described above. More preferably, the concentration of the borane-tetrahydrofuran complex is at least 1.5 M. Most preferably, the concentration of the borane-tetrahydrofuran complex is at least 2.0 M.

Preventing escape of diborane from the system provides a number of advantages, including more efficient use of reagents by higher reactor loading; less formation of by-products during reaction; and eliminating the need to use excess borane-tetrahydrofuran complex.

DETAILED DESCRIPTION OF THE INVENTION

Figure 1:
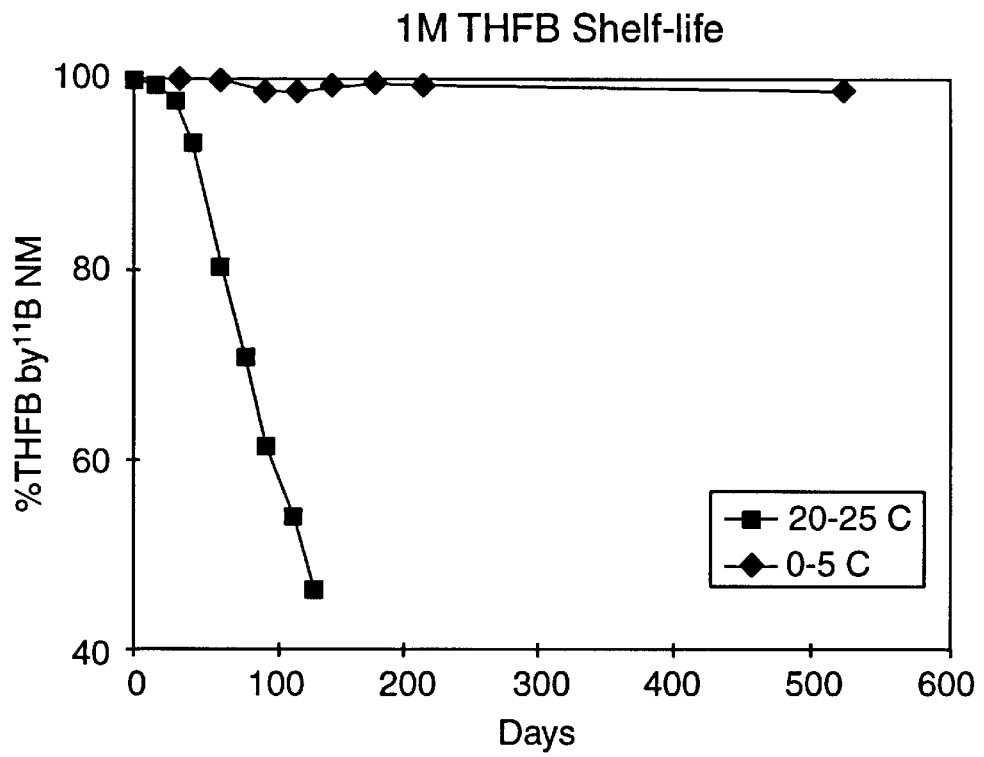
FIG. 1 illustrates a shelf-life or decomposition study of 1 M THFB at ambient temperature and at a temperature in the range of 0 to 5° C.

Until the present invention it was believed that greater than 1 M THFB is not viable for use commercially because of its instability. Surprisingly, the present inventors have discovered that greater than 1 M THFB can be synthesized and is stable for long periods when stored at temperatures cooled below ambient temperature.

Prior attempts to synthesize relatively highly concentrated THFB used an in situ preparation of THFB. See U.S. Pat. No. 3,634,277. Major drawbacks are encountered during the in situ preparation of borane-tetrahydrofuran complex from sodium borohydride (the cheapest and most available borohydride) and boron trifluoride. For example, stirring of the thick slurry of sodium tetrafluoroborate which forms during the reaction can be difficult. Secondly, if the reaction is filtered before all the boron trifluoride has been consumed, it may contaminate the solution. Third, the sodium tetrafluoroborate is a fine powder and very difficult to filter from the solution of borane-tetrahydrofuran complex. Moreover, the amount of excess borohydride determines the quantity of stabilizing agent (identified as $B_3H_8^-$ $Na^+$ by $^{11}B$ NMR spectroscopy) in the borane-tetrahydrofuran complex solution which can be highly variable.

Instead of an in situ route to the borane-tetrahydrofuran complex in tetrahydrofuran, in the present invention borane-tetrahydrofuran complex is preferably made in high purity by addition of diborane to the solvent, tetrahydrofuran. A known amount of sodium borohydride is preferably added to stabilize the borane complex. Unlike the case of prior, in situ methods, the amount of stabilizing agent, $B_3H_8^-Na^+$, is the same for each production batch when diborane is added to tetrahydrofuran to form THFB.

The diborane used in the present invention is preferably stored at temperatures less than −100° C. (the boiling point of diborane is −92.5° C.). Such cryogenic storage allows one to safely preserve large quantities of diborane for use at a later time. Any solvent or reaction by-products (except for non-condensable gas such as nitrogen or methane) which inadvertently arrive at the storage vessel are frozen and do not escape. Therefore, the diborane withdrawn from a cryogenic storage vessel is of higher purity (typically greater than 99%, as sampled from liquid diborane) than that produced directly from the gas stream of a reactor (typically 95–97.5% purity). Furthermore the impurities are exclusively non-condensable, non-reactive gases, whereas diborane taken directly from a reactor can contain ether solvents, alkylboranes, borates, alkylboronic esters and borontrifluoride complexes. Thus, preparation of borane reagents from cryogenically stored diborane yields higher purity borane reagents than when produced by in situ routes.

Addition of diborane from a storage vessel such as a cylinder or directly from diborane generated in another reaction vessel to tetrahydrofuran generates the borane-tetrahydrofuran complex of high purity and high concentration. The concentration of borane-tetrahydrofuran complex per liter of tetrahydrofuran can, for example, range up to approximately 10 M. More preferably, the concentration is in the range of approximately 1.0 M to approximately 6.0 M. Even more preferably, the concentration is in the range of approximately 1.0 M to approximately 2.5 M. Most preferably, the concentration is approximately 2.0±0.1 M.

The complex formation is mildly exothermic, therefore, cooling of the reaction vessel is preferred. The temperature of the tetrahydrofuran during the diborane addition is preferably in the range of approximately −20° C. to approximately 20° C. with a preferred temperature of 0 to 15° C.

Sodium borohydride or another hydride ($H^-$) source (for example, potassium borohydride, lithium borohydride, tetraalkylammonium borohydride and alkali metal hydrides such as LiH, KH, and NaH) can be added to the solution as stabilizers. Other methods to generate the stabilizing reagent include addition of metal alkoxides to the solution. Various metal alkoxides can be chosen, including, but not limited to, sodium tert-butoxide, potassium tert-butoxide, lithium tert-butoxide, sodium tert-amylate, potassium tert-amylate, lithium tert-amylate, sodium isopropoxide, potassium isopropoxide, lithium isopropoxide, sodium methoxide, potassium methoxide, or lithium methoxide.

To preserve the purity of the borane-tetrahydrofuran complex, packaged solutions should be kept below ambient temperature, and preferably below approximately 20° C. Most preferably, the temperature is in the range of approximately −20° C. to approximately 5° C.

Thermal decomposition of borane-tetrahydrofuran complex (THFB) occurs by ether cleavage of the tetrahydrofuran ring. Tributylborate ($(BuO)_3B$) is ultimately the end product after all the borane (B—H bonds) has reacted. The following reaction scheme illustrates the reaction.

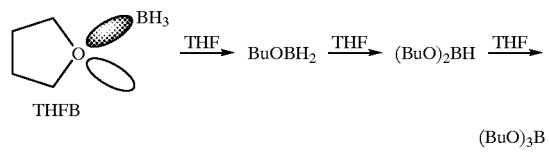

$$\text{THFB} \xrightarrow{\text{THF}} BuOBH_2 \xrightarrow{\text{THF}} (BuO)_2BH \xrightarrow{\text{THF}} (BuO)_3B$$

At the moderately cold temperatures of the present invention, it has been discovered that the ether cleavage of THF by THFB is quite slow. Indeed, shelf-life studies on 1 M THFB stored at 0 to 5° C. have demonstrated that very little decomposition occurs over 1.5 years. After this time period the THFB had lost only 1% of its activity. The shelf-life of 2M THFB is also very good when stored at 0 to 5° C. After 318 days the 2M THFB had lost only 2% of its THFB. The amount of THFB in the solution was measured by $^{11}B$ NMR spectroscopy. At ambient temperature, 1 M borane-tetrahydrofuran complex degrades by about 50% over 120 days, while 2 M THFB degrades by 50% over about 60 days.

In that regard, Table 1 sets forth data from a of 2 M THFB maintained at ambient temperature (20 to 25° C.), while Table 2 sets forth data from a cylinder of 2 M THFB maintained at 0 to 5° C. for the duration of a "shelf-life" test.

TABLE 1

| Hydrolysis | | $^{11}B$ NMR | | | |
|---|---|---|---|---|---|
| Day | mol/l by H | THFB | $(BuO)_3B$ | $(BuO)_2BH$ | Other |
| 1 | 1.92 | 98.2 | 0.8 | 0.01 | 1 |
| 3 | 2.00 | 97.9 | 0.8 | 0.01 | 1.3 |
| 7 | 1.98 | 96.9 | 0.9 | 0 | 2.2 |
| 16 | 1.93 | 96.7 | 1.6 | 0.6 | 1.1 |
| 24 | 1.89 | NA | NA | NA | NA |
| 29 | 1.85 | 93 | 2.7 | 3.2 | 1.9 |
| 44 | 1.65 | 73 | 11 | 10 | 3 |
| 50 | NA | 65 | 17.4 | 12.4 | 5 |
| 71 | NA | 39 | 37 | 20 | 5 |
| 110 | NA | 15.6 | 60 | 19 | 5.4 |

TABLE 2

| Hydrolysis | | $^{11}B$ NMR | | | |
|---|---|---|---|---|---|
| Day | mol/l by H | THFB | $(BuO)_3B$ | $(BuO)_2BH$ | Other |
| 1 | 1.92 | 98.2 | 0.8 | 0.01 | 1 |
| 50 | NA | 98 | 1 | 0.01 | 1 |
| 74 | 1.98 | 97.2 | 1 | 0.3 | 1.5 |
| 90 | 1.95 | 97.4 | 1.1 | 0.3 | 1.2 |
| 140 | 2.04 | 97.4 | 1 | 0.4 | 1.2 |
| 182 | NA | 98.1 | 1 | 0.1 | 0.8 |
| 230 | NA | 98.3 | 1 | 0.1 | 0.7 |
| 318 | 1.89 | 96.3 | 1.7 | 0.9 | 1.0 |

Figure 2:
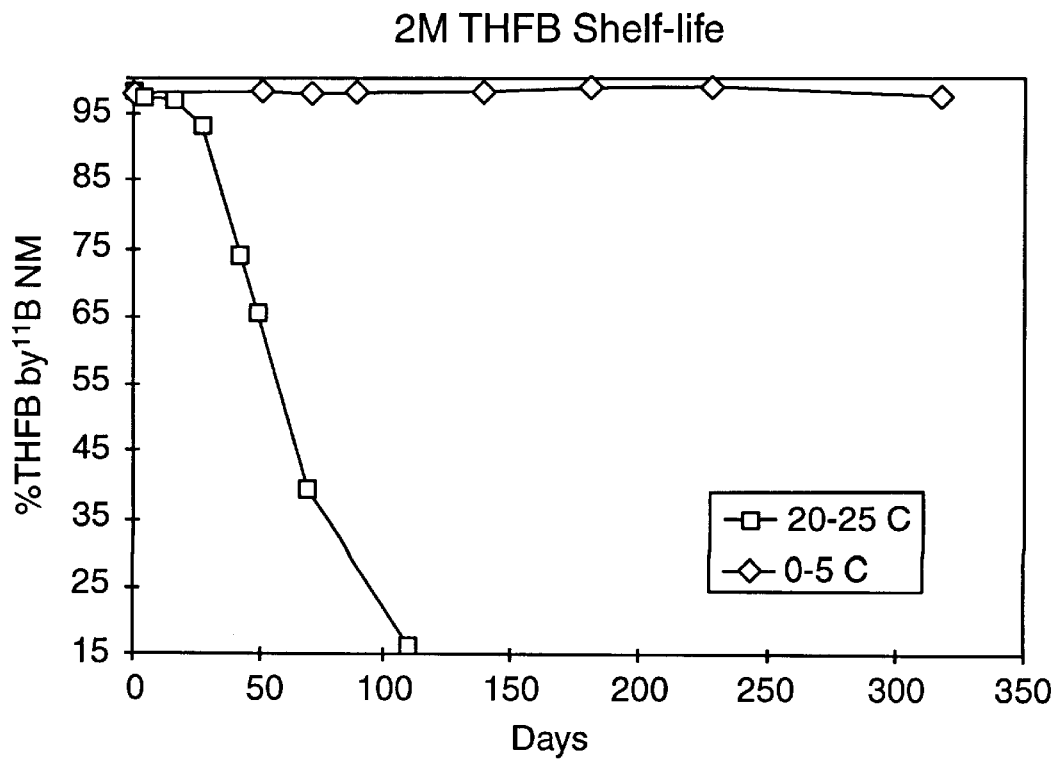
FIG. 2 illustrates a shelf-life or decomposition study of 2 M THFB at ambient temperature and at a temperature in the range of 0 to 5° C.

FIG. 1 illustrates the results of shelf-life tests for 1 M THFB at ambient temperature and at 0 to 5°, while FIG. 2 illustrates shelf-life tests for 2 M THFB at temperature and at 0 to 5°.

In the absence of substrate in a reactor system (that is, when excess borane reagent is used), borane-tetrahydrofuran complex can decompose by two independent pathways. At temperatures below 50° C., the decomposition pathway is by tetrahydrofuran ring-opening (ether cleavage) as illustrated above. In addition to ether cleavage, decomposition by loss of diborane is observed at elevated temperatures (for example, between 50° C. and 66° C.; the boiling point of tetrahydrofuran is 66° C.). Near the boiling point of THF the dominant pathway leading to decreased hydride activity is loss of diborane. When the reactor system is at one atmosphere and open to a scrubber system the diborane can escape.

In the presence of substrate, borane-tetrahydrofuran complex reacts readily and preferentially with the desired compound and ring opening is a minor pathway generating insignificant amounts of tributylborate. In the event that excess borane-tetrahydrofuran complex is used in the reaction and the reaction mixture is heated, the remaining borane-tetrahydrofuran complex can cleave the THF and/or leave the system as diborane.

Figure 3:
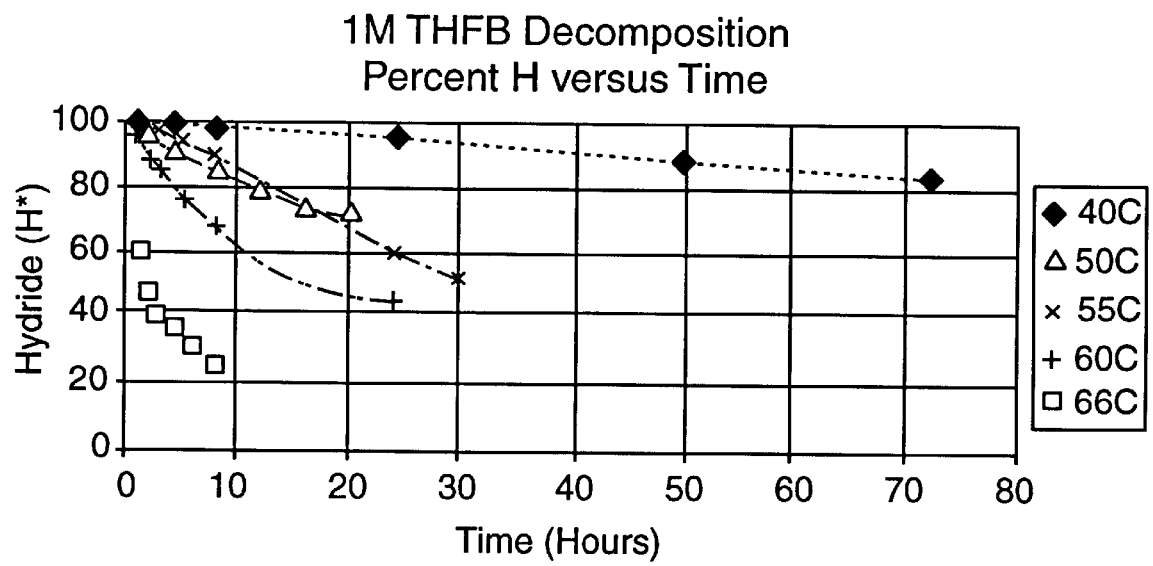
FIG. 3 illustrates a plot of percent hydride ($H^-$) versus time at various temperatures.

The thermal decomposition of THFB at elevated temperatures was initially studied by heating a THFB solution in a temperature-controlled bath in a round-bottomed flask under nitrogen at atmospheric pressure. Samples were taken at intervals and analyzed by titration of the remaining active hydride (H$^-$) and by $^{11}B$ NMR to determine the extent of conversion to butyl borate. The active hydride titration measures all borane and borohydride species. The $^{11}B$ NMR spectrum allows quantification of THFB relative to dibutoxyborane, tributylborate and boron hydride ($BH_n$) species. The intermediate monobutoxyborane is never observed in the solution by $^{11}B$ NMR spectroscopy. FIG. 3 illustrates a plot of active hydride (H$^-$) versus time and demonstrates the loss of activity.

The exact reaction mechanism of thermal decomposition has not been determined. The overall decomposition does not follow first or second order kinetics. Several possible mechanistic routes can be envisioned. The ether cleavage reaction could be unimolecular where the coordinated borane adds the hydrogen in a four center transition state with concomitant carbon-oxygen bond scission. Alternatively in a bimolecular reaction pathway, uncoordinated borane may attack a THF molecule possibly coordinated to a Lewis acid (such as $BH_3$, $BF_3$, $(RO)_3B$).

Figure 4:
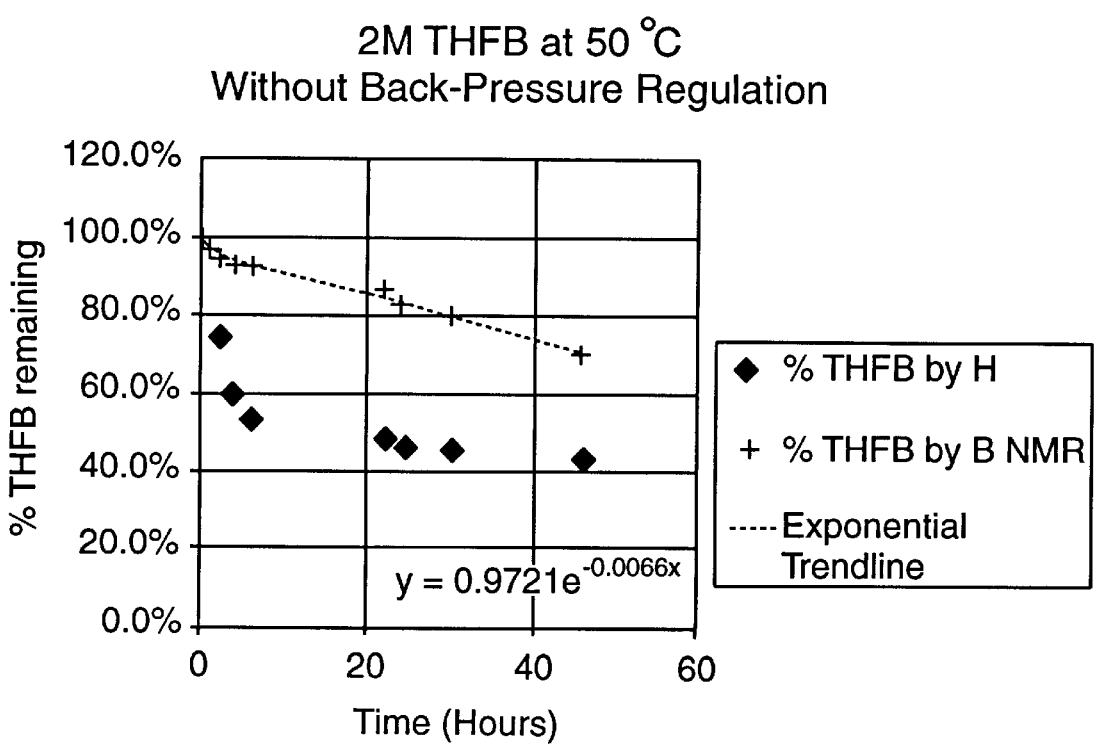
FIG. 4 illustrates a decomposition study of 2 M THFB at approximately 50° C. without back-pressure regulation.

In the course of conducting thermal decomposition studies on 1 M borane-tetrahydrofuran complex (THFB), loss of reagent (borane as the dimer, diborane) from the solution was observed when heated under one atmosphere of nitrogen at temperatures above 55° C. The phenomenon was seen during the 2M THFB thermal studies above 50° C. and is even more pronounced. By plotting H⁻versus time and percent remaining THFB versus time on the same plot as illustrated in FIG. 4, one observes a divergence at these higher temperatures.

Even taking into account that the active hydride (H⁻) measurement shows THFB and a small contribution from $(BuO)_2BH$ and any borohydride species, the measured value was much lower than the mole fraction of THFB observed in the $^{11}B$ NMR spectra. It is believed that this divergence is a result of the loss of diborane from the heated solution. Indeed, methyl borate was observed in the methanol scrubber to which the reactor system was attached. The amount of methyl borate corresponded to the amount of borane lost from the system.

To keep the borane in the reactor system, the reaction can, for example, be carried out in a closed system such as an autoclave or in a vessel with a pressure regulating device (for example, a back-pressure regulator) to act as a safety vent.

Figure 5:
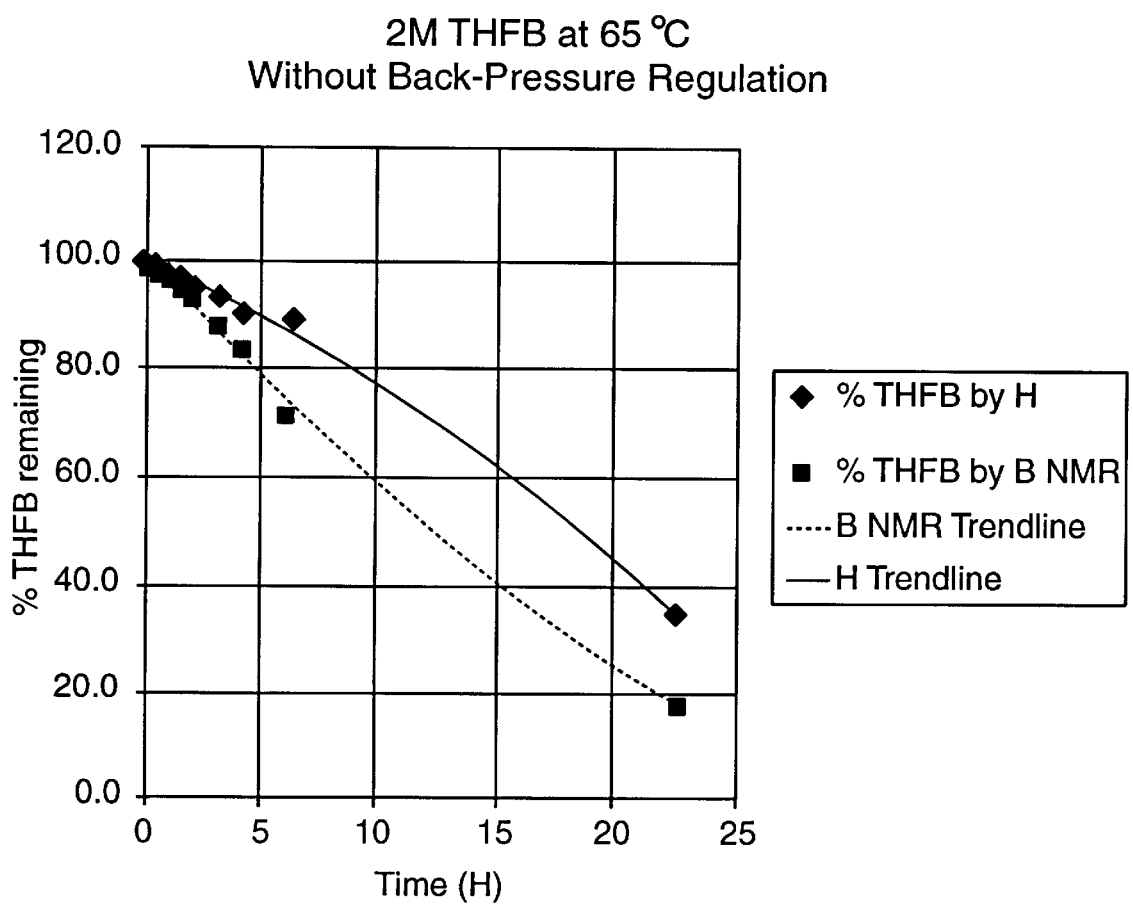
FIG. 5 illustrates a decomposition study of 2 M THFB at approximately 65° C. with back-pressure regulation.
Figure 6:
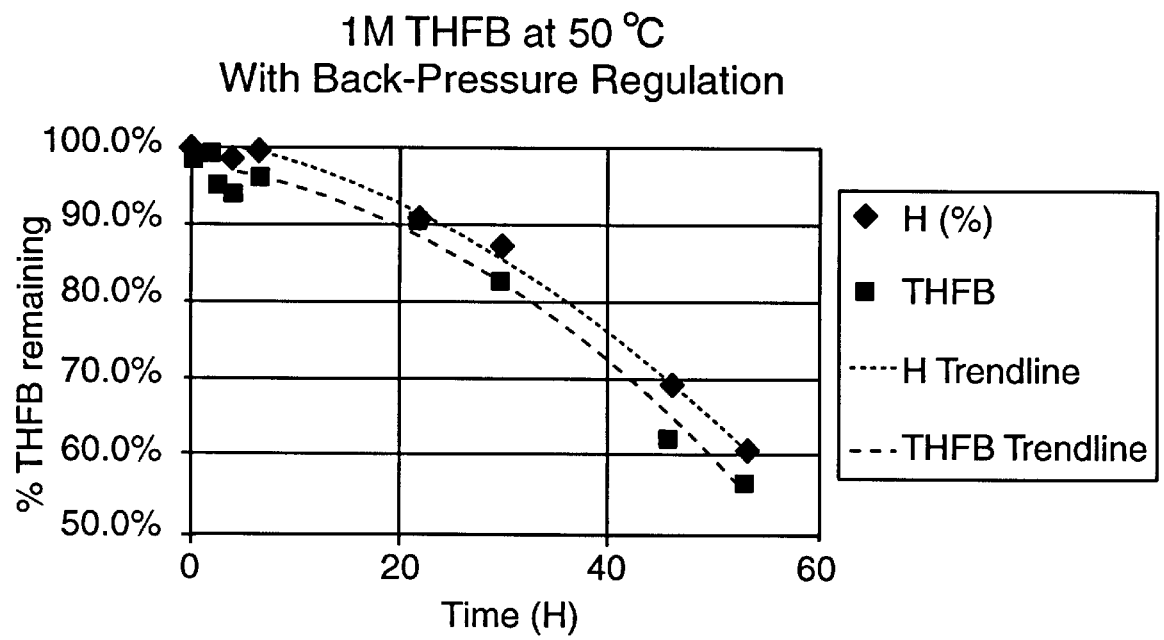
FIG. 6 illustrates a decomposition study of 2 M THFB at approximately 50° C. with back-pressure regulation.

In one experiment using the present invention, the ether cleavage of tetrahydrofuran by borane-tetrahydrofuran complex was investigated. Borane-tetrahydrofuran complex (2M THFB) was heated at 65° C. in a sealed Fisher-Porter bottle fitted with a back-pressure regulator set at 40 psig. The pressure in the vessel rose to about 20 psig during the heating period. Because of the pressure in the vessel, the THF does not reflux. Samples were taken periodically for analysis by $^{11}B$ NMR and hydride titration. The ether cleavage of THF correlates well with the consumption of hydride activity, demonstrating that borane is not lost from the system. The results of this experiment are illustrated in FIG. 5. A similar experiment with 2M THFB at 50 ° C. sealed in a Fisher-Porter bottle confirmed that diborane is not lost from the system. The results of this experiment are illustrated in FIG. 6.

Figure 7:
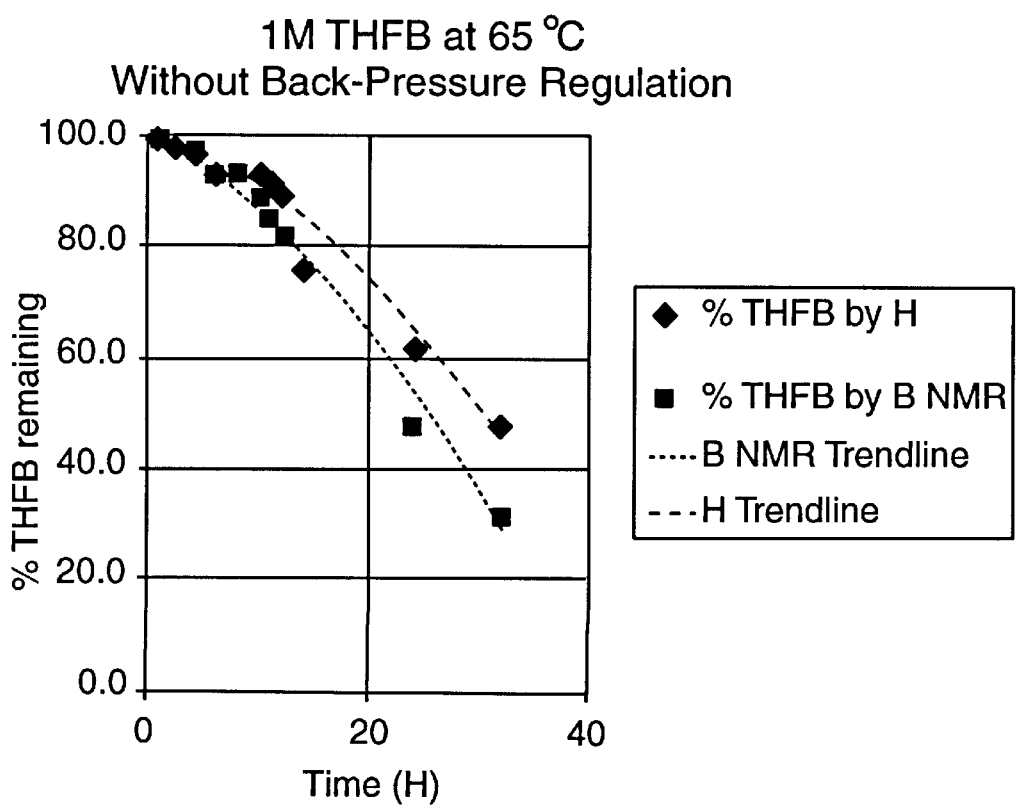
FIG. 7 illustrates a decomposition study of 1 M THFB at approximately 65° C. with back-pressure regulation.

In an analogous experiment with 1M THFB at 65° C., it has been demonstrated that reactions with 1M THFB also benefit from elevated pressure in the reactor system. The results of this experiment are illustrated in FIG. 7.

In all the reactions in which the THFB (1M or 2M) was heated in a reactor under pressure, the diborane did not escape. Any reaction containing THFB has the potential to loose diborane when heated. Using a system with a back pressure regulating device allows the reaction to be run under pressure and contains all of the borane reagent so that it is available for the desired reaction.

As discussed above, borane reagents, and especially borane-tetrahydrofuran complex, are extremely useful for the reduction of aldehydes, ketones, esters, carboxylic acids, amides, nitriles, lactones, lactams and epoxides. Hydroboration of carbon-carbon double bonds with borane reagents will produce mono-, di-, or trialkyl-borane compounds depending on the olefin and amount used. Hydroboration of triple bonds with borane reagents gives either vinylic boron compounds or alkylboranes containing two boron atoms. Synthesis of other borane reagents such as catechol borane, pinacol borane and diisopropoxyborane can also be accomplished using THFB. Many of these reactions are conducted at elevated temperatures. When using borane reagents at or above ambient temperatures (for example a lactone, lactam, oxime, or amide reduction and hydroboration of bulky olefins), some of the reagent could potentially be lost from the system. Any diborane which leaves the system is not available for reaction with the substrate, therefore additional THFB would be needed to complete the desired reaction. Such reactions at elevated temperatures would benefit from being conducted under pressure as described in the present invention.

EXAMPLE 1

Shelf-life testing. Tetrahydrofuran (802.3 g, 900 mL) was loaded into a pressure reactor. A back-pressure regulator was set at 20 psig and the reactor immersed in a water bath at 10° C. Diborane (27 g, 0.98 mol) from a cylinder was added over two hours. Sodium borohydride (0.3 g) was added to the borane-tetrahydrofuran complex. The clear solution was transferred to two mild steel cylinders for the shelf-life testing. The density of the solution was 0.872 g/ml at 21° C. The initial analysis of the solution showed 98% THFB by $^{11}B$ NMR spectroscopy. Titration of the solution showed the concentration to be 1.92M.

Table 1 above shows the data from the cylinder kept at ambient temperature (20 to 25 ° C.). Table 2 above shows the data from the cylinder kept at 0 to 5° C. for the duration of the shelf-life test.

EXAMPLE 2

One gallon scale. Tetrahydrofuran (2800 g, 3160 mL) and sodium borohydride (1.6 g) were loaded into a 1 gallon stainless steel pressure reactor. A back-pressure regulator was set at 30 psig. The reactor was chilled to 0 to 5° C. with a circulating coolant. Diborane (87.7 g, 3.17 mol) from a cylinder was added over 2 hours and 50 minutes to give a 2.09 M solution of borane-tetrahydrofuran complex. The density of the solution was 0.875 g/ml at 24.5° C. The $^{11}B$ NMR spectrum showed 99% THFB and 1% $NaB_3HB$. The contents of the reactor was filtered and packaged in steel cylinders.

EXAMPLE 3

Synthesis of highly concentrated THFB for use in the preparation of catechol borane. Tetrahydrofuran (306 g, 350 mL) was loaded into a pressure reactor. A back-pressure regulator was set at 20 psig and the reactor immersed in a water bath at 0C. Diborane (28g, 1.01 mol) from a cylinder was added over two hours and 10 minutes to give a 5.8 M solution of borane-tetrahydrofuran complex. Catechol (178.4 g, 1.62 mol) dissolved in tetrahydrofuran (167 g) was slowly added to the solution of borane-tetrahydrofuran complex over 2.5 hours. The resulting solution of catechol borane in tetrahydrofuran displayed the expected doublet at 24 ppm in the $^{11}B$ NMR spectrum. The concentration was determined to contain 5.42 M catechol borane by hydrogen evolution measurement and had a density of 1.0934 g/mL at 24° C.

EXAMPLE 4

Use of high concentration THFB for the preparation of [3.3.1]-9-borabicyclononane (9-BBN). THFB (100 mL, 2.1M) was placed in a 1 liter 3-necked-round bottom flask equipped with addition funnel, condenser, thermocouple and nitrogen inlet. 1,5-Cyclooctadiene (22.7 g) was added via the addition funnel over one hour. The mixture was then heated to reflux for 2.5 hours to complete the reaction. The $^{11}B$ NMR spectrum of the solution showed 9-BBN at δ 29 ppm plus a small amount of trialkylborane. Upon cooling the solution, crystals of 9-BBN precipitated from solution.

EXAMPLE 5

Thermal decomposition. Thermal decomposition tests at one atmosphere were conducted under nitrogen as follows.

The THFB solution was placed into a round bottom flask fitted with a condenser, nitrogen inlet and thermocouple. The flask was immersed into a temperature controlled water bath to maintain a constant temperature. Any exiting gas from the reaction was past through a methanol scrubber, thus allowing for the determination of diborane loss.

Samples of the solution were removed from the flask at intervals for analysis by $^{11}$B NMR spectroscopy and titration to determine the remaining hydride (H$^-$). The following tables show the data for 1M THFB.

TABLE 3

Data for THFB at 40° C.

| Time (Hrs) | % H |
|---|---|
| 0 | 100 |
| 1 | 99.7 |
| 4 | 98.8 |
| 8 | 98.2 |
| 24 | 95.5 |
| 50 | 89.8 |
| 72 | 84.1 |

TABLE 4

Data for % THFB at 50° C.

| Time (Hrs) | % H |
|---|---|
| 0 | 100 |
| 2 | 95.1 |
| 4 | 90.2 |
| 8 | 84.5 |
| 12 | 78.4 |
| 16 | 73.3 |
| 20 | 71.3 |

TABLE 5

Data for % THFB at 55° C.

| Time (hrs) | % H | $^{11}$B NMR |
|---|---|---|
| 0 | 100 | 100 |
| 1 | 99.7 | 100 |
| 2 | 98.8 | 99 |
| 3 | 97.0 | 99 |
| 5 | 93.8 | 97 |
| 8 | 89.3 | 95 |
| 24 | 58.9 | 65 |
| 30 | 51.5 | 54 |

TABLE 6

Data for % THFB at 60° C.

| Time (Hrs) | % H |
|---|---|
| 0 | 100 |
| 1 | 94.4 |
| 2 | 86.4 |
| 3 | 85.2 |
| 5 | 76.3 |
| 8 | 67.8 |
| 24 | 44.4 |

TABLE 7

Data for % THFB at 66° C.

| Time (hrs) | % H | $^{11}$B NMR |
|---|---|---|
| 0 | 100 | 100 |
| 1 | 60.0 | 99.3 |
| 2 | 46.4 | NA |
| 3 | 38.2 | 97.2 |
| 4 | 36.4 | 96.8 |
| 6 | 29.6 | 94.4 |
| 8 | 24.3 | 83.3 |

EXAMPLE 6

Thermal decomposition. The procedure of Example 5 was also used to collect data for 2M THFB at one atmosphere.

EXAMPLE 7

Thermal decomposition. Thermal decomposition tests under pressure were conducted in a Fisher-Porter bottle equipped with a back-pressure regulator. The back-pressure regulator was set at 40 psig to hold the gas in the vessel but allow a safety emergency release of excess pressure. The vessel was immersed into a temperature controlled water or oil bath to maintain a constant temperature.

Samples of the solution were removed from the flask at intervals for analysis by $^{11}$B NMR spectroscopy and titration to determine the remaining hydride. Table 8 presents the data for the thermal degradation of THFB (1.05 M) at 65° C. with a 40 psig back-pressure. The internal vessel rose to 20 psig.

TABLE 8

1M THFB at 65° C.

| | | | Percent by $^{11}$B NMR | | | |
|---|---|---|---|---|---|---|
| Time (h) | H$^-$ (M) | H$^-$ (%) | THFB | (BuO)$_2$ BH | (BuO)$_3$ B | other |
| 0 | 1.05 | 100.0 | 99.1 | — | — | 0.9 |
| 0.5 | 1.04 | 99.0 | 99.0 | — | — | 1.0 |
| 1 | 1.04 | 99.0 | 99.0 | — | — | 1.0 |
| 1.5 | 1.03 | 98.1 | 98.9 | — | — | 1.1 |
| 2 | 1.02 | 97.1 | 98.7 | — | — | 1.3 |
| 3 | 1.02 | 97.1 | 97.8 | — | 0.8 | 1.4 |
| 4 | 1.01 | 96.2 | 97.3 | 0.5 | 0.8 | 1.4 |
| 6 | 0.985 | 93.8 | 92.9 | 1.2 | 1.7 | 4.2 |
| 8 | 0.976 | 93.0 | 93.1 | 1.8 | 0.7 | 4.3 |
| 10 | 0.972 | 92.6 | 89.0 | 4.4 | 1.2 | 5.37 |
| 11 | 0.957 | 91.1 | 84.9 | 6.3 | 1.5 | 7.23 |
| 12 | 0.936 | 89.1 | 82.3 | 8.3 | 2.0 | 7.51 |
| 24 | 0.646 | 61.5 | 47.7 | 27 | 15 | 9.96 |
| 32 | 0.5 | 47.6 | 31.8 | 32 | 24.6 | 11.6 |

EXAMPLE 8

Thermal decomposition. According to the procedure in Example 7 for reactions under 40 psig pressure, the following data were collected for THFB (2.0 M) at 50° C.

TABLE 9

2M THFB at 50° C.

| | | | Percent by $^{11}$B NMR | | |
|---|---|---|---|---|---|
| Time (h) | H$^-$ (M) | H$^-$ (%) | THFB | (BuO)$_2$BH | (BuO)$_3$B | other |
| 0 | 2.01 | 100.0 | 98.1 | — | — | 1.88 |
| 1 | 2.05 | 102.0 | 99.0 | — | — | 1.00 |
| 2 | 2.05 | 102.0 | 98.9 | — | — | 1.11 |
| 3 | 2.03 | 101.0 | 94.6 | — | 2.65 | 2.75 |
| 4 | 1.98 | 98.5 | 94.1 | — | 3.33 | 2.59 |
| 6.5 | 2.00 | 99.5 | 95.9 | 0.54 | 2.06 | 1.48 |
| 22 | 1.82 | 90.5 | 90.8 | 3.91 | 1.14 | 4.10 |
| 29.5 | 1.76 | 87.6 | 82.9 | 8.75 | 2.92 | 5.40 |
| 46 | 1.40 | 69.7 | 62.9 | 18.4 | 9.60 | 9.16 |
| 53 | 1.23 | 61.2 | 57.0 | 21.8 | 13.20 | 7.98 |
| 53h + 2d RT | 1.14 | 56.7 | 53.4 | 20.6 | 20.10 | 5.87 |

EXAMPLE 9

Thermal decomposition. According to the procedure in Example 7 for reactions under 40 psig pressure, the following data were collected for THFB (2.0 M) at 40° C.

TABLE 10

2M THFB at 40° C.

| | | | Percent by $^{11}$B NMR | | |
|---|---|---|---|---|---|
| Time (h) | H$^-$ (M) | H$^-$ (%) | THFB | (BuO)$_2$BH | (BuO)$_3$B | other |
| 0 | 2.01 | 100.0 | 98.1% | — | — | 1.9 |
| 1 | 2.16 | 107.5 | 98.2 | 0.0 | 0.0 | 1.8 |
| 2 | 2.04 | 101.5 | 99.3 | 0.0 | 0.0 | 0.7 |
| 3.5 | 2.05 | 102.0 | 98.5 | 0.0 | 0.0 | 1.5 |
| 20 | 2.05 | 102.0 | 97.4 | 0.5 | 1.1 | 1.4 |
| 27.5 | 2.00 | 99.5 | 92.9 | 2.0 | 1.9 | 3.2 |
| 43.75 | 1.92 | 95.5 | 81.6 | 8.8 | 3.3 | 6.4 |
| 51 | 1.83 | 91.0 | 76.8 | 11.8 | 4.7 | 6.7 |
| 68 | 1.66 | 82.6 | 63.7 | 18.7 | 9.8 | 7.8 |
| 74 | 1.57 | 78.1 | 59.8 | 20.0 | 12.5 | 7.7 |
| 92 | 1.33 | 66.2 | 48 | 24.7 | 19.7 | 7.5 |
| 98 | 1.24 | 61.7 | 45.3 | 25.6 | 22.2 | 6.9 |
| 98 + 2d RT | 1.23 | 61.2 | 41.9 | 22.4 | 28.2 | 7.5 |

EXAMPLE 10

Thermal decomposition. According to the procedure in Example 7 for reactions under 40 psig pressure, the following data were collected for THFB (2.0 M) at 65° C.

TABLE 11

2M THFB at 65° C.

| | | | Percent by $^{11}$B NMR | | |
|---|---|---|---|---|---|
| Time (h) | H$^-$ (M) | H$^-$ (%) | THFB | (BuO)$_2$BH | (BuO)$_3$B | other |
| 0 | 2.00 | 100 | 98.6 | — | — | 1.4 |
| 0.5 | 2.00 | 100 | 97.5 | — | — | 2.5 |
| 1 | 1.96 | 98.0 | 96.3 | — | 2.0 | 1.7 |
| 1.5 | 1.95 | 97.5 | 95.3 | 0.6 | 2.2 | 1.9 |
| 2 | 1.91 | 95.5 | 93.4 | 0.9 | 1.3 | 4.4 |
| 3 | 1.86 | 93.0 | 88.0 | 3.3 | 1.2 | 7.5 |
| 4 | 1.80 | 90.0 | 83.4 | 7.3 | 1.8 | 7.6 |
| 6 | 1.78 | 89.0 | 71.2 | 14.6 | 3.7 | 10.5 |
| 22.5 | 0.69 | 34.5 | 18.1 | 28.9 | 38.3 | 14.7 |

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A method of stabilizing borane-tetrahydrofuran complex, the method comprising the step of maintaining the temperature of the borane-tetrahydrofuran complex at or below 20° C. for an extended period of time.

2. The method of claim 1 wherein the temperature is maintained above cryogenic temperatures.

3. The method of claim 1 wherein the borane-tetrahydrofuran complex has a concentration of borane-tetrahydrofuran complex per liter of tetrahydrofuran above 1 M.

4. The method of claim 2 wherein the temperature is maintained in the range of approximately −20° C. to 20° C. for an extended period of time.

5. The method of claim 4 wherein the temperature is maintained in the range of approximately −20° C. to 15° C. for an extended period of time.

6. The method of claim 2 wherein the temperature is maintained at a temperature at or below 5° C. for an extended period of time.

7. The method of claim 6 wherein the temperature is maintained in the range of approximately −20° C. to 5° C. for an extended period of time.

8. The method of claim 1 wherein the borane-tetrahydrofuran complex has a concentration of borane-tetrahydrofuran complex per liter of tetrahydrofuran of at least 1.5 M.

9. The method of claim 2 wherein the borane-tetrahydrofuran complex has a concentration of borane-tetrahydrofuran complex per liter of tetrahydrofuran of at least 2.0 M.

10. The method of claim 6 wherein the borane-tetrahydrofuran complex has a concentration of borane-tetrahydrofuran complex per liter of tetrahydrofuran of at least 1.5 M.

11. The method of claim 6 wherein the borane-tetrahydrofuran complex has a concentration of borane-tetrahydrofuran complex per liter of tetrahydrofuran of at least 2.0 M.

12. The method of claim 2 wherein the borane tetrahydrofuran complex is produced by adding diborane to tetrahydrofuran.

13. A method of reacting a borane reagent with a substrate, the method comprising the steps of heating the borane reagent and the substrate in a reaction vessel and preventing escape of evolved diborane from the reaction vessel.

14. The method of claim 13 wherein the borane reagent is borane-tetrahydrofuran complex.

15. A method of reacting a borane reagent with a substrate, the method comprising the steps of heating the borane reagent and the substrate in a reaction vessel and maintaining the reaction vessel under a pressure of greater than atmospheric pressure.

16. The method of claim 15 wherein the reaction vessel is maintained under a pressure in the range of approximately 5 psig to approximately 100 psig.

17. The method of claim 15 wherein the borane-tetrahydrofuran complex has a concentration of borane-tetrahydrofuran complex per liter of tetrahydrofuran above 1 M and the borane-tetrahydrofuran complex is stored before reaction thereof at a temperature at or below 20° C.

18. The method of claim 17 wherein the borane-tetrahydrofuran complex is stored before reaction thereof at a temperature above cryogenic temperatures.

19. The method of claim 18 wherein the borane-tetrahydrofuran is stored before reaction thereof at a temperature in the range of approximately −20° C. to 5° C.

20. The method of claim 15 wherein the concentration is at least 2.0 M.

\* \* \* \* \*